United States Patent [19]

Keppel et al.

[11] 4,091,019

[45] May 23, 1978

[54] PREPARATION OF UNSATURATED PRIMARY AMINES

[75] Inventors: Robert A. Keppel, University City; John S. McConaghy, Jr., St. Louis, both of Mo.

[73] Assignee: Monsanto Company, St. Louis, Mo.

[21] Appl. No.: 680,569

[22] Filed: Apr. 27, 1976

[51] Int. Cl.² ............... C07C 85/145; C07C 87/24
[52] U.S. Cl. ............... 260/585 R; 252/429 B; 252/431 P; 260/583 H
[58] Field of Search ........... 260/593 H, 585 R, 583 R; 252/431 P, 429 B

[56] References Cited

U.S. PATENT DOCUMENTS 3,110,731  11/1963  Boswell .................. 260/583 H
3,865,877  2/1975   Arpe et al. ............. 260/583 H

OTHER PUBLICATIONS

Spialter and Papalardo, "The Acyclic Aliphatic Tertiary Amines", pp. 34, 35 & 36 (1965).

*Primary Examiner*—Daniel E. Wyman
*Assistant Examiner*—John J. Doll
*Attorney, Agent, or Firm*—J. C. Logomasini; P. L. Passley; S. M. Tarter

[57] ABSTRACT

A process for the production of unsaturated primary amines which comprises reacting, in the substantial absence of molecular oxygen, an amine having the formula $(R_1HC=CR_2CH_2)_m NH_{(3-m)}$, wherein m is 2 or 3 and $R_1$ and $R_2$ are hydrogen or $C_1 - C_3$ alkyl groups, with ammonia in the presence of a catalyst comprising palladium or platinum atoms bearing phosphorus-containing ligands, the reaction being carried out at a temperature of from 0° to 250° C in the presence of a solvent for the amine and the catalyst.

8 Claims, No Drawings

PREPARATION OF UNSATURATED PRIMARY AMINES

BACKGROUND OF THE INVENTION

This invention relates to a process for the preparation of unsaturated primary amines from the corresponding secondary and tertiary amines.

Allylamine is probably the most useful of the unsaturated primary amines to which the invention relates since it is a valuable intermediate in the production of a number of pharmaceuticals, herbicides and plastics.

One of the problems in the production of primary amines is that almost invariably, unless produced by the reduction of a cyanide group, they are not obtained pure but in substantial admixture with secondary and tertiary amines. In fact, most frequently secondary and tertiary amines form the bulk of the production.

The present invention provides an efficient and convenient means for converting the secondary and tertiary amines into primary amines.

One solution to this problem involves disproportionation of the secondary amine to primary and tertiary amines. Thus U.S. Pat. No. 3,865,877 discloses disproportionating diallylamine to monallylamine and triallylamine.

Another method disclosed in an article in Ang. Chem. Int. Edit, 12, p928 (1973), shows the reaction of triallylamine with formic acid to give allyl formate, diallylamine, monoallylamine, propane and carbon monoxide. This is, however, a most uneconomic route since the by-products are many and predominant.

It is, therefore, clear that a process for converting secondary and tertiary unsaturated amines to the monounsaturated amine would be a very useful addition to the art.

SUMMARY OF THE INVENTION

The present invention provides a process for the production of unsaturated primary amines which comprises reacting, in the substantial absence of molecular oxygen, an amine having the formula $(R_1HC=CR_2CH_2)_mNH_{(3-m)}$, wherein $m$ is 2 or 3 and $R_1$ and $R_2$ are hydrogen or $C_1 - C_3$ alkyl groups, with ammonia in the presence of a catalyst comprising palladium or platinum atoms bearing phosphorus-containing ligands, the reaction being carried out at a temperature of from 0° to 250° C in the presence of a solvent for the amine and the catalyst.

The reaction that takes place in the process of the invention is essentially an allyl group transfer reaction and while such reactions have been described in the literature in, for example, U.S. Pat. No. 3,755,451 and Chemical Communications 1392 (1970), the use of ammonia as a component in such a reaction, in effect as an acceptor of an allyl group, is quite unexpected in view of the known low reactivity of the ammonia molecule in such reactions. The catalyst useful in the process of the reaction consists essentially of platinum or palladium atoms bearing phosphorus-containing ligands. The ligands serve a dual function. In the first place, they permit the reaction to be carried out in the liquid phase, (a preferred feature of this invention). In the second place, they protect the metal from becoming deactivated during the reaction. Ammonia forms particularly strong, stable complexes with both palladium and platinum and this not only reduces the amount of ammonia in the reaction but also prevents the catalyst from operating effectively. It is found that phosphorus-containing ligands are sufficiently tightly bonded to the metal to preclude displacement by ammonia except at very high pressures and yet do not interfere with the catalyst's catalytic activity.

The catalyst may be formed in situ as for example if palladium of platinum metal absorbed on a solid support is placed in a suitable solvent along with the phosphorus containing ligand material, the ligands form a soluble metal complex with the adsorbed metal. More commonly, however, the palladium or platinum metal or compound is added to the ligand material in a separate reaction and the resulting catalyst is separated and added to the reaction vessel.

It is preferred that the metal atom in the catalyst be in the zero-valent state though this is not an essential feature of the invention since it found that catalysts containing the metal in the divalent state are also effective though to a lesser extent.

One particular group of catalysts in which the metal is apparently in a divalent state are certain $\pi$-complexes of palladium (II), such as those described in U.S. Pat. No. 3,584,020. These complexes are, however, themselves able to react with ammonia as is described in detail in U.S. Pat. No. 3,642,902 and it is believed that, in the process, a zero-valent complex of palladium is obtained and this catalyses the reaction of the ammonia with the amine. Regardless of theory, it is intended that the use of such $\pi$-complexed catalysts be embraced within the purview of this invention along with other platinum and palladium compounds such as palladium chloride, palladium acetate, platinum chloride and the like, in the form of complexes having phosphorous-containing ligands. The preferred catalysts however have zero-valent palladium or platinum complexed with phosphorus containing ligands having the formula $R'_3P$ where the three $R'$ groups may be the same or different hydrocarbyl or hydrocarbyloxy groups such as phenyl, tolyl, phenoxy, methoxy, ethoxy, butoxy or cyclohexoxy groups or where two of the $R'$ groups may be linked to form a bidentate ligand such as bis(1,2-diphenylphosphino) ethane.

Typical catalysts that are effective in the process of the invention include tetrakis (tributoxyphosphine) palladium, tetrakis (triethoxyphosphine) palladium, tetrakis(triphenylphosphine) platinum, tetrakis(triphenylphosphine) palladium, and bis[bis(1,2-diphenylphosphino)ethane] palladium. In general palladium complexes perform better than the corresponding platinum complexes.

The ligands linked to the metal comprise a phosphorus atom and though in theory it is recognized the arsenic and antimony analogues could be substituted, such alternatives are not considered as effective or economic.

The ratio of phosphorus to palladium or platinum in the preferred catalyst can be any that will maintain the catalyst in solution and in practice this means at least 3:1 and preferably 4:1, but it can, of course, be much higher.

The amount of catalyst used, based on the amine reactant can be in a molar ratio of catalyst to amine of up to 1:1 but effective results are obtained with a molar ratio as low as 1:10,000 and most suitably of about 1:100.

The secondary and tertiary unsaturated amines that may be reacted in the process of the invention are those having the general formula $(R_1HC=CR_2-CH_2-)_mNH_{(3-m)}$ wherein $m$ is 2 or 3 and $R_1$ and $R_2$ are either hydrogen or $C_1 - C_3$ alkyl groups. Thus the amine reactants can be secondary or tertiary amines containing allyl, methallyl, ethallyl, propallyl, 2-methyl-allyl, 2-ethyl-allyl, 2-propylallyl, 2-methyl-methallyl, 2-propyl-methallyl or 2-ethyl-propallyl groups. For the sake of convenience, all such compounds are hereafter resumed collectively under the designation "allylamines".

The reaction is performed in the presence of a solvent for both the amine and the catalyst and it is found that various solvents can be used. These may include ethers such as tetrahydrofuran, aromatic or aliphatic hydrocarbons such as o-xylene and n-hexane or esters such as ethyl acetate. Better solvents include methylated amides such as N-methylpyrrolidone; ketones such as 2-butanone; water; pyridine and dimethyl sulfoxide. The best solvents for most purposes are alcohols particularly $C_1$ to $C_6$ alcohols such as butanol or pentanol and including polyalcohols such as propylene glycol and glycerol. The preferred alcohols are $C_2 - C_6$ polyalcohols.

An important novel aspect of this invention is the discovery that certain compounds enhance the reaction quite markedly. In general, ammonium salts of acids (which salts may be formed "in situ") such as ammonium chloride and ammonium acetate have been found to be particularly active promoters of the reaction. The promoter can be present in any efficacious amount but usually the molar ratio of promoter to catalyst is from 1:10 to 1,000:1 and preferably from 1:1 to 10:1.

The reaction is usually performed at a temperature of from 0° to 200° C such as from 25° to 150° C. While some promoters are more effective at slightly higher temperatures than others, in general the preferred range is from 50° to 150° C. It is found that if the temperature is elevated to a point outside the above broad range, the problem of catalyst decomposition has to be considered.

The reaction may be performed at any convenient pressure and, while it is found that the reaction is enhanced by the use of superatmospheric pressure, care must be taken to avoid the use of very high pressures, (in effect of ammonia), since these tend to deactivate the catalyst by displacement of ligands from the metal. In general, pressures from subatmospheric to as high as 50 kg/cm² can be used though a pressure range of from atmospheric up to 15 kg/cm² is preferred in practice.

If the above reaction is performed using e.g., a triallylamine and ammonia, one of the first reaction products is of course a diallylamine which will thereafter react with more ammonia to produce the monoallylamine. It is found, however, that there is another mechanism by which a diallylamine may be converted to a monoallylamine. Using the same reaction conditions and the same catalyst system, diallylamines are found to disproportionate to mono- and tri-allylamines and of course the tri-allylamine will react according to the process of the invention to give more diallylamine.

The reactions going on in the reaction vessel are of course equilibrium reactions and as is usual in such cases, the monoallylamine can be fractioned off to displace the position of the equilibrium in the desired direction.

Frequently in the production of allylamines, a mixture of the mono-, di- and tri- products is obtained so that such mixtures may be conveniently subjected directly to the process of the invention.

SPECIFIC EMBODIMENTS

The invention is further illustrated by the following Examples. In Examples 1 to 7, the catalyst used is palladium or platinum complexed with a phosphorus-containing ligand.

In Examples 8 to 11, the catalyst is in the form of an allyl palladium chloride in which the palladium is apparently in the divalent state. It is, however, theorized that, in the presence of the phosphorus containing ligand, this complex first reacts with ammonia to generate allylamine, hydrogen chloride (which becomes ammonium chloride through reaction with ammonia) and zero valent palladium metal which thereafter combines with the added phosphorus-containing ligand material to form a Pd° complex similar to that used in Examples 1-6. Regardless of theory, it is found that comparable results are obtained using such a catalyst system.

EXAMPLE 1

A 300 ml autoclave was charged with 5.8g (5 millimoles) of tetrakis (triphenylphosphine) palladium, 1.8g (13.3 millimoles) of triallylamine and 80ml of N-methyl pyrrolidone as a solvent. Oxygen was removed from the autoclave by a nitrogen purge and then ammonia was added with stirring until the internal pressure reached 3.87 Kg/cm. The reactor was then heated with stirring to 100° C (pressure - 10.19 kg/cm) and subsequently to 130° C (pressure - 13.34 kg/cm). At 100° C the reaction was very slow but after 30 minutes at 130° C the triallylamine had reacted to form 5.2 millimoles of monoallylamine and 6.6 millimoles of diallylamine.

EXAMPLE 2

Example 1 was duplicated with the difference that 2.1g (40 millimoles) of ammonium chloride were added to the autoclave and the temperature was raised only to 100° C. After one hour at 100° C, 8.8 millimoles of monoallylamine and 8.4 millimoles of diallylamine had been formed.

EXAMPLE 3

Example 2 was duplicated except for the use of pyridine as the solvent. After 100 minutes at 100° C., 4.2 millimoles of monoallylamine and 6.6 millimoles of diallylamine had been formed.

EXAMPLE 4

An autoclave was charged with 0.58g (0.5 millimoles) of tetrakis (triphenylphosphine) palladium 1.82g (13.3 millimoles) of triallylamine, 0.11g (2 millimoles) of ammonium chloride and 80ml of 1-butanol. After a nitrogen purge to remove the oxygen, the autoclave was pressured to 3.52 kg/cm² with ammonia. It was then heated to 100° C (pressure 10.19 kg/cm²) and after 15 minutes at this temperature it was found that 11 millimoles of monoallylamine and 9 millimoles of diallylamine had been formed.

EXAMPLE 5

Example 4 was duplicated with the difference that 20 millimoles of diallylamine was substituted for triallylamine as the starting material. A sample taken when the temperature had just reached 100° C showed 2.8 millimoles of monoallylamine and 2.2 millimoles of triallylamine showing that some disproportionation had occurred. After 30 minutes at 100° C the sample showed 13 millimoles of monoallylamine and 3.3 millimoles of triallylamine. The triallylamine content continued to diminish with increasing time under the reaction conditions.

EXAMPLE 6

An autoclave was charged with a solution of 0.44g (0.38 millimoles) of tetrakis(triphenylphosphine) palladium and 0.12g (2.3 millimoles) of ammonium chloride in 30 ml of 1-pentanol. The autoclave was purged with nitrogen, then heated to 100° C with stirring at which point 1.95g. (14.2 millimoles) of triallylamine and sufficient ammonia to maintain a pressure of 10.19 kg/cm² were added. After 45 minutes the stirred reaction mixture comprised 3.6 millimoles of monoallylamine, 7.0 millimoles of diallylamine and 8.2 millimoles of triallylamine. After 90 minutes, the respective amounts were 7.8, 9.0 and 5.6 millimoles and after 4 hours, the amounts were 10.3, 9.2 and 4.7 millimoles respectively.

EXAMPLE 7

An autoclave was charged with a solution of 0.35g (0.28 millimoles) of tetrakis (triphenylphosphine) platinum and 0.098g (1.8 millimoles) of ammonium chloride in 25 ml of 1-pentanol. The autoclave was purged with nitrogen then the mixture was heated with stirring to 100° C at which point 1.5g (10.9 millimoles) of triallylamine and sufficient ammonia to maintain a pressure of 10.19 kg/cm² were added. After 30 minutes the stirred reaction mixture comprised 5.3 millimoles of monoallylamine, 6.5 millimoles of diallylamine and 4.5 millimoles of triallylamine.

EXAMPLES 8-10

An autoclave was charged with a solution of allyl palladium chloride and triethoxyphosphine in 80 ml of 1-pentanol. The autoclave was purged with nitrogen, then heated to 100° C with stirring at which point triallylamine and sufficient ammonia to maintain a pressure of 8.08 kg/cm² were added.

Samples of the reaction mixture were analyzed during the reaction and the results are set forth in Table 1 below.

cent diallylamine and 28 mole percent triallylamine. After 90 minutes of stirring the mole percentages for mono-, di- and tri- allylamine were 44, 39 and 17, respectively. After 18 hours, mono-, di- and tri-allylamine molar percentages were 46, 38 16 respectively. More than 95% of the allyl groups were retained in the mixed allylamines.

What we claim is:

1. A process for the production of unsaturated primary amines which comprises reacting an amine having the formula $(R_1HC{=}CR_2{-}CH_2)_m NH_{(3-m)}$ wherein "m" is 2 or 3 and $R_1$ and $R_2$ are each hydrogen or $C_1$ to $C_3$ alkyl groups with ammonia in the presence of a catalyst comprised of zero-valent palladium or platinum atoms bearing phosphorus-containing ligands and a catalyst promoter selected from the group consisting of ammonium acetate and ammonium chloride in a molar ratio of promoter to catalyst that is from 1:1 to 10:1, the reaction being carried out at a temperature of from 0° C. to 250° C. in the substantial absence of molecular oxygen and in the presence of a solvent for the amine.

2. A process according to claim 1 in which the catalyst is zero-valent palladium or platinum having phosphorus-containing ligands attached thereto wherein the ratio of phosphorus to platinum or palladium atoms is from 3:1 to 4:1.

3. A process according to claim 1 in which the phosphorus-containing ligands have the formula $R_3 P$ wherein the three R groups are the same or different hydrocarbyl- or hydrocarbyloxy-groups.

4. A process according to claim 1 in which the reaction is performed at a temperature of from 25° C to 150° C and a pressure of from atmospheric up to 15 kg/cm².

5. A process according to claim 1 in which the reaction is performed in solution in an alcohol.

6. A process for the production of monoallylamine which comprises reacting, in the substantial absence of molecular oxygen and in alcoholic solution, di- or triallylamine with ammonia at a pressure of from atmospheric up to 15 kg/cm² and a temperature of from 25° C to 150° C in the presence of a catalyst having the formula $Pd° [R_3P]_4$ wherein R is an aryl, aryloxy, $C_1$-$C_6$ alkyl or a $C_1$-$C_6$ alkoxy group and a promoter selected from ammonium acetate and ammonium chloride.

7. A process according to claim 6 in which the catalyst is selected from tetrakis [triphenylphosphine] palladium, tetrakis [tributoxyphosphine] palladium and tetrakis [triethoxyphosphine] palladium.

8. A process according to claim 6 in which the reaction takes place in solution in $C_2$-$C_6$ polyalcohol.

TABLE 1

| Example | Tri AA Charged | Allyl Pd.Cl(g) | (EtO)₃P (g) | Added Accelerator (g) | Reaction Mixture Analysis in Millimoles | | | |
|---------|----------------|----------------|-------------|----------------------|----------------------------------------|---------|-------|-------|
| | | | | | Time (mins) | Mono AA | Di AA | Tri AA |
| 8 | 9.2g (67mM) | 0.037 (0.20mM) | 0.10 (0.62mM) | — | 120 | 6.2 | 14.8 | 54.5 |
| | | | | | 165 | 7.0 | 16.2 | 53.2 |
| 9 | 9.2g (67mM) | 0.036 (0.20mM) | 0.97 (0.58mM) | 4.6g (60mM) ammonium acetate | 120 | 10.4 | 22.5 | 48.1 |
| | | | | | 300 | 17.7 | 30.5 | 40 |
| 10 | 9.3g (67.8mM) | 0.036 (0.20mM) | .098 (0.58mM) | 0.11g (21.mM) ammonium chloride | 120 | 7.5 | 17.2 | 53.8 |
| | | | | | 180 | 10.5 | 23.9 | 48.4 |

Allyl Pd Cl - allyl palladium chloride
(EtO)₃P - triethoxy phosphine
mM - millimoles
Tri AA - triallylamine
Di AA - diallylamine
Mono AA - monoallylamine

EXAMPLE 11

An autoclave was charged with a solution of 0.25g (1.34 millimoles) of allyl palladium chloride, 1.36g (5.45 millimoles) tributylphosphite, 1.92g (14.0 millimoles) of triallylamine and 0.83g (13.8 millimoles) of acetic acid in 75 ml of propylene glycol. The autoclave was then purged with nitrogen and heated to 100° C with stirring at which point 9.94g (72.5 millimoles) of triallylamine were added and sufficient anhydrous ammonia to maintain a pressure of 8.08 kg/cm². After 30 minutes of stirring at 100° C, sufficient triallylamine had reacted with ammonia to give a solution of allylamines which consisted of 30 mole percent allylamine, 42 mole per-